United States Patent
Scordilis (10) Patent No.: US 8,823,547 B2
(45) Date of Patent: Sep. 2, 2014

(54) APPARATUS AND METHODS FOR SEARCHING AND SELECTING AN RF TELEMETRY CHANNEL TO ESTABLISH A LINK WITH AN ACTIVE MEDICAL DEVICE

(75) Inventor: Thierry Scordilis, Poisat (FR)

(73) Assignee: Sorin CRM S.A.S., Clamart Cedex (FR)

( * ) Notice: Subject to any disclaimer, the term of this patent is extended or adjusted under 35 U.S.C. 154(b) by 744 days.

(21) Appl. No.: 13/111,854

(22) Filed: May 19, 2011

(65) Prior Publication Data

US 2011/0285545 A1 Nov. 24, 2011

(30) Foreign Application Priority Data

May 19, 2010 (FR) ...................................... 10 53858

(51) Int. Cl.
G08C 19/06 (2006.01)
(52) U.S. Cl.
USPC ........................................ 340/870.05; 607/60
(58) Field of Classification Search
CPC ........... A61N 1/37223; A61N 1/37252; A61N 1/37276; H04B 1/713; Y02B 60/50
USPC .......... 340/1.1–3.71, 870.01–870.44; 607/32, 607/60; 375/132; 128/903–904
See application file for complete search history.

(56) References Cited

U.S. PATENT DOCUMENTS

| | | | |
|---|---|---|---|
| 6,441,747 B1 | 8/2002 | Khair | |
| 6,868,288 B2 | 3/2005 | Thompson | |
| 7,663,451 B2 | 2/2010 | Dal Molin | |
| 2006/0161223 A1* | 7/2006 | Vallapureddy et al. | 607/60 |
| 2006/0247736 A1* | 11/2006 | Roberts | 607/60 |
| 2007/0049983 A1* | 3/2007 | Freeberg | 607/32 |
| 2007/0060053 A1* | 3/2007 | Haubrich et al. | 455/39 |
| 2007/0185550 A1* | 8/2007 | Vallapureddy et al. | 607/60 |
| 2008/0015655 A1 | 1/2008 | Bange | |
| 2008/0015656 A1* | 1/2008 | Bange et al. | 607/32 |
| 2008/0055070 A1* | 3/2008 | Bange et al. | 340/539.12 |
| 2008/0264431 A1* | 10/2008 | Masoud et al. | 128/899 |
| 2009/0252042 A1* | 10/2009 | Bradley et al. | 370/241 |
| 2010/0036463 A1* | 2/2010 | Bange et al. | 607/60 |
| 2010/0121414 A1* | 5/2010 | Roberts | 607/60 |
| 2010/0168819 A1* | 7/2010 | Freeberg | 607/60 |
| 2010/0249881 A1* | 9/2010 | Corndorf | 607/60 |

FOREIGN PATENT DOCUMENTS

EP 1862195 A1 12/2007
WO WO 2007/114743 A1 10/2007

OTHER PUBLICATIONS

Annexe Au Rapport De Recherche Preliminaire Relatif A La Demande De Brevet Francais No. FR 1053858 FA 738089, Jan. 20, 2011.

* cited by examiner

Primary Examiner — Hai Phan
Assistant Examiner — Orlando Bousono
(74) Attorney, Agent, or Firm — Foley & Lardner LLP (57) ABSTRACT

An apparatus and method for searching and selecting an RF telemetry channel to establish a link between an active medical device and a remote device is disclosed. In the absence of any communication request, the available communication channels are scanned periodically to perform a long-term analysis. For each channel, a long-term indicator (iCLT) that is representative of a long-term availability is generated. Upon receipt of a communication request from the remote device, the communication channels are scanned to perform a short-term analysis, a short-term indicator (iCCT) that is representative of the short-term availability is generated. The short-term indicator is weighted by the long-term indicator, to generate a weighted short-term indicator (iCP). Based on the weighted short-term indicator, a communication channel is selected as the communication channel for the communication request.

10 Claims, 4 Drawing Sheets

FIG. 6

APPARATUS AND METHODS FOR SEARCHING AND SELECTING AN RF TELEMETRY CHANNEL TO ESTABLISH A LINK WITH AN ACTIVE MEDICAL DEVICE

The present application claims the benefit of French application No. 10/53858 entitled "Process for search and selection of an RF telemetry channel to establish a link with an active medical device" and filed May 19, 2010, which is hereby incorporated by reference in its entirety.

FIELD

The present invention relates to "active medical devices" as defined by the directive 93/42/CE of Jun. 14, 1993 of the European Community Council, and preferably to "active implantable medical devices" as defined by the directive 90/395/CEE of Jun. 20, 1990 of the European Community Council, including devices for monitoring cardiac activity and generating electrical pulses for the stimulation, resynchronization, defibrillation and/or cardioversion of a patient's heart in response to an arrhythmia detected by the devices, or any other devices such as neurological devices, pumps for diffusion of medical substances, cochlear implants, implanted biological sensors, and devices for measuring pH or intracorporeal impedance (e.g., transpulmonary impedance measurement and intracardiac impedance). It should be understood that the present invention is advantageously applicable to implanted devices (e.g., pacemakers, cardioverter or defibrillators) and non-implanted devices (e.g., data recorders, Holter devices) intended for ambulatory monitoring and recording of physiological parameters of a patient such as cardiac activity signals.

BACKGROUND

Some active medical devices are designed to exchange data signals with a remote device, commonly referred to as a "programmer." The remote device is often a separate external device used to verify the configuration of the coupled device, read information recorded by the device, post information to the device, and update the operational parameters of the device. The data exchange between the medical device and the programmer is done via telemetry, by remote transmission of information without galvanic contact therebetween.

For implantable medical devices, existing data transmission via telemetry is often conducted by an inductive coupling between the coils of the implanted device and those of the programmer. However, this inductive coupling technique has a disadvantage, because of the requirement of physical proximity between the implanted device and the programmer and a "telemetry head" connected to the programmer such that an operator places the coils of the programmer in the vicinity of the site where the device is implanted to establish inductive coupling.

Recently, a non-galvanic and non-inductive coupling technique was proposed for data communication via electromagnetic wave between two components operating in a radiofrequency (RF) domain, typically in the frequency range of several hundred Megahertz. This technique, referred to as "RF telemetry" allows programming or interrogating an implanted device at a distance greater than 3 m from a programmer, thus it enables exchange of data without a telemetry head, or even without an intervention by an external operator.

One active medical device employing such an RF telemetry system is described in EP 1862195 A1 and its counterpart U.S. Pat. No. 7,663,451 (both assigned to Sorin CRM S.A.S., previously known as ELA Medical). The communication protocol between an active device (which may be but is not necessarily an implantable device) and its base station (e.g., a programmer or a "home monitor" device) is governed by the industry standard EN 301 839, Electromagnetic Compatibility and Radio Spectrum Matters (ERM)—Short range devices (SRD)—Ultra Low Power Active Medical Implants (ULP-AMI), and Peripherals (ULP-AMI-P), operating in the frequency range of 402-405 MHz. It is noted, however, that the RF telemetry system described herein is not limited to the 402-405 MHz frequency band for Medical Implants Communication Systems ("MICS"), but is generally applicable to any bands that could be used for the RF telemetry, including, for example, the Industrial, Scientific and Medical (ISM) public unmarked bands 863-870 MHz, 902-928 MHz, or 2.4 GHz, as may be used by medical devices.

Moreover, medical devices equipped with RF telemetry functions are generally multichannel devices using multiple frequencies in one band, but some devices may also be multiband.

Therefore, prior to establishing communication between an active device and its base station (programmer), it is necessary to select a channel (i.e., a communication frequency) among those available channels in the given frequency band. This step is important because it is essential to select with confidence a channel having a noise level such that the communication can be carried to completion without being interrupted.

Unlike induction telemetry techniques that have generally good noise immunity, the RF telemetry technique is subject to numerous electromagnetic disturbances, including radio, television and mobile phone signals, or industrial or environmental noises that may be present in the vicinity of the patient. The device, particularly when communicating on an RF channel, can also be in conflict with other nearby devices trying to connect in the same RF channel. All these disturbances are likely to cause interferences and disrupt the data transmission. If an RF channel that is too noisy is selected, the data communication is subject to transmission errors, leading to the abandonment of the process and the search for a new channel. It may be required to repeat the communication process until a successful communication is established, and consequently it causes energy loss for the unsuccessful communication attempts. RF telemetry involves relatively high energy consumption, at a significant scale for an implantable device whose useful life is critical, so that multiple interrupted communications can pose a significant impact on the autonomy of the device.

When selecting a communication channel, an initial or previous scan is involved to successively "listen" to the various available channels for transmission, before choosing one of them to start broadcasting signals.

U.S. Pat. No. 6,868,288 B2 describes a technique for selecting a communication channel by simultaneously analyzing the average received signal level on each channel, and then classifying these channels according to the respective detected signal level. Any signal detected on a given channel is considered as noise. Each selected channel is then analyzed separately to verify that it is available when the device starts to emit signals. However, between the moment of the scan and the start of data transmission, communication may have started on that same channel from another device, so that the selected channel may actually be occupied and no longer available.

This technique of channel selection based on simultaneous scan and subsequent analysis for channel selection based on the signal level has two main drawbacks. First, because of the selected analysis criterion, any signal present in the selected channel is regarded as noise. In other words, the analysis does not distinguish between background noise (i.e., "real" noise) and a valid communication data signal on this channel: the latter is regarded by the device as noise, while this data communication may take place on a quality channel in terms of Signal Noise Ratio (SNR). In other words, the device may exclude such a quality channel, only due to the fact that this channel is occupied at the moment of the scan.

Secondly, during the signal scan, the analysis of an average signal level on a given channel does not guarantee the availability of the channel when the device begins to broadcast data signals on that channel. The risk of an inability to establish successfully data communication remains, and in such cases the established communication channel needs to be switched to another channel by repeating the process, resulting in an increased loss of energy.

It should be understood that this risk is particularly aggravated in a hospital environment where multiple devices are simultaneously present from the same manufacturer using the same channel selection algorithms. For example, multiple devices may try to establish an RF communication channel at moments relatively close in time, and because of this slight temporal shift, a first device may consider a channel is free, while another device starts to emit a little time later and make communication impossible for the first device, forcing it to repeat the channel scan to search for another channel. The presence of a plurality of products of the same origin in the same site may cause unexpected interference with each other, requiring an operation logic with complex escaping loops.

This phenomenon is further enhanced by the relatively high overall occupancy of various channels in a clinical environment, but the problem of finding an available channel is superimposed on the problem of finding a noisy channel.

U.S. Pat. Publication No. US2008/015655 A1 (Bange & Al.) describes a comparable technique but with the same drawbacks; it is impossible to assess the risk of establishing a channel that has a low noise level at a given moment but is not the optimal channel at another moment when it is really to be used, and so throughout its use.

OBJECTIVES AND SUMMARY

It is, therefore, an objective of the present invention to provide an RF communication channel search and selection technique that can distinguish between a busy channel and a channel with a significant level of background noise to identify channels with good SNR even if they are busy, so those channels can later be used when they become available.

It is another objective of the present invention to propose a technique for analysis and selection of a channel to maximize the likelihood of establishing a connection and continue the selected connection until desired data transmission is completed.

In one embodiment, the present invention is directed to selecting not only a clear and noisy channel at the time of scanning, but also a channel that is likely to be available at the moment when the device attempts to establish communication with a remote device. By maximizing the likelihood to establish, maintain, and complete the required data communication on that selected channel on the first attempt, the overall amount of energy needed to transfer information between the implanted device and the base station is reduced, optimizing the battery life of the device.

Another objective of the present invention is to propose a technique that requires only modest resources in terms of computing power, involving only simple algorithms, or even a logic that could be implemented as hardware using comparators and/or threshold circuits, in a particularly advantageous manner with the limited resources available in an active implantable medical device.

In one embodiment of the present invention, a technique is provided for seeking and selecting a communication channel prior to establishing an RF telemetry link with a remote device, said method being of a general type, for example, described in the aforementioned U.S. Pat. Publication No. US2008/015655 A1, comprising:

in the absence of a communication request or of a communication in progress with the remote device, conducting a periodic scanning and a first analysis of the plurality of channels and, for each channel, determining and storing at least one long-term indicator representative of long-term availability; and upon receipt of a request for communication with the remote device, conducting a second analysis of the plurality of channels and, for each channel, determining and storing of at least one short-term indicator representative of short-term availability; weighting the short-term indicator by the stored long term indicator, to obtain a weighted short-term indicator; and selecting one of said plurality of channels as the communication channel based on said weighted short-term indicator.

In a preferred embodiment, the first or second analysis includes a step of comparing a signal level of each channel to a predetermined baseline noise threshold level. This allows, for each channel whose signal level is above the baseline noise level, to perform a signal type discrimination step, for differentiating a useful data signal frame and a real noise signal. In one embodiment, this discrimination step further applies a low-pass filtering to the signal during a temporal window of a predetermined duration, and compares between the filtered signal and the unfiltered signal to give a first signal type indicator. In another embodiment, the discrimination step further detects a signal peak level, and compares between the signal peak and the filtered signal to give a second signal type indicator.

Another embodiment of the invention is directed to an apparatus for communication with a remote device comprising:

an attenuator for receiving signals on a plurality of channels from the remote device;

a channel filter for selectively receiving signals on a selected channel of the plurality of channels; and a means for searching and selecting a communication channel among the plurality of channels, prior to the establishment an RF telemetry link with the remote device, wherein the means for searching and selecting establishes the RF telemetry link comprises:

means for a first analysis, the first analysis being periodically conducted for each channel of said plurality of channels;

means for determining and storing a first indicator representative of a long-term availability for each channel of the plurality of channels;

means for a second analysis, the second analysis being conducted for each channel of said plurality of channels in response to a communication request from the remote device;

means for determining and storing a second indicator representative of a short-term availability for each channel of the plurality of channels; and means for selecting the communication channel from said plurality of channels based on said first and second indicators.

wherein said first indicator is a long-term indicator representative of the long-term availability;

wherein the second indicator is a short-term indicator representative of the short-term availability;

wherein a weighted short-term indicator is generated by weighting of the short-term indicator by the long-term indicator; and wherein said communication channel is selected based on the weighted short-term indicator.

Preferably, the means for the first or second analyses further comprises means for comparing a signal level of each channel to a predetermined threshold level of baseline noise. In a preferred embodiment, the means for the first or second analyses further comprises, for each channel whose signal level is above the predetermined threshold level of baseline noise, means for discriminating a signal type by differentiating a data frame signal and a noise signal. Preferably, the means for discriminating a signal type further comprises a low-pass filter filtering the received signals over a temporal window of a predetermined duration; a comparator for comparing the filtered signal and the unfiltered signal; and means for generating a first indicator of signal type based on the comparison of the filtered signal and the unfiltered signal. Further, the means for discriminating preferably comprises: peak signal level detector; a comparator for comparing the signal peak level and the filtered signal; and means for generating a second indicator of signal type based on the comparison of the peak signal level and the filtered signal.

BRIEF DESCRIPTION OF THE DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements, and in which.

DETAILED DESCRIPTION

Figure 1:
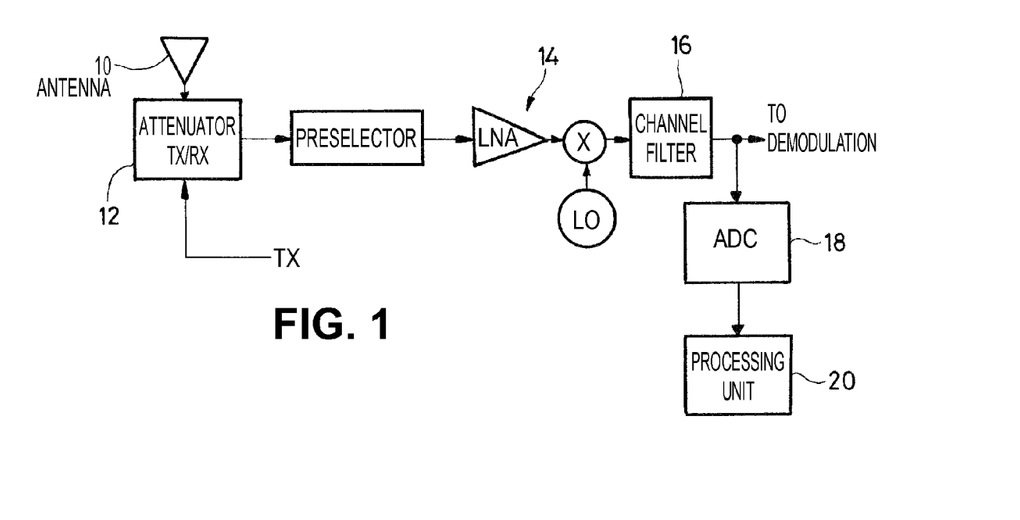
FIG. 1 illustrates a schematic diagram of a reception circuit of an active medical device, according to one embodiment.

Various embodiments of the present invention will be described with reference to the drawings. FIG. 1 illustrates a schematic diagram of a reception circuit (i.e., receiver) of an active medical device (e.g., an implantable device or a base station). The signals collected from RF antenna 10 are applied to attenuator 12 controlled by a signal TX. Specifically, during an already established communication, attenuator 12 is set to "RX" for a reception mode with minimum attenuation. In contrast, in a first scanning and analysis phase of the channel scanning, when the signal level on a given channel is unknown, attenuator 12 is switched to "TX" for a transmission mode. The switch to the "TX" mode occurs even when the device continues to operate in the reception mode to avoid saturating the downstream stages or circuits. The condition that triggers the switch back to Rx mode depends on the sensitivity of the reception circuit, for example, saturation of the RX chain with respect to the level of the RSSI. If the level of RSSI is greater the saturation level, attenuator 12 remains at Tx mode whereas if the level of RSSI is lower than the saturation level, attenuator 12 switches back the RX mode to benefit from a maximum sensitivity.

The signal collected is applied to a series of high frequency stages 14, comprising in sequence, a preselector that operates to pass only the frequency band of interest and allows the receiver to be protected from other RF emissions, a low noise amplifier (LNA) that is used to increase the signal/noise ratio (SNR), a local oscillator (LO), and a mixer (X). In one embodiment, the receiver of FIG. 1 is a classical RF receiver of a super-heterodyne architecture. The resulting intermediate frequency signal out of the high frequency stages 14 is applied to channel filter 16 (also known as a notch filter) corresponding to the selected channel passing only the signal components present in the channel of interest. For example, channel filter 16 has a bulk acoustic wave (BAW) resonator as described in EP1862195/U.S. Pat. No. 7,663,451 referenced above.

The receiver configuration of FIG. 1 is advantageous in that it can freeze the circuit and capture the desired frequency, simply by changing the frequency of the local oscillator LO. A focus is made on the digitization of the signal received from channel filter 16 allowing a central processing unit with associated memory registers ("CPU") of the active medical device to process the corresponding digitized signal on a channel by channel basis.

The signal at the output of channel filter 16, which is normally applied to a demodulation circuit as part of an already established communication, is used to detect the signal level after being applied to analog/digital converter (ADC) 18 and to CPU 20. The operation of ADC 18 and CPU 20 is described in detail with reference to FIGS. 2 and 3.

Figure 2:
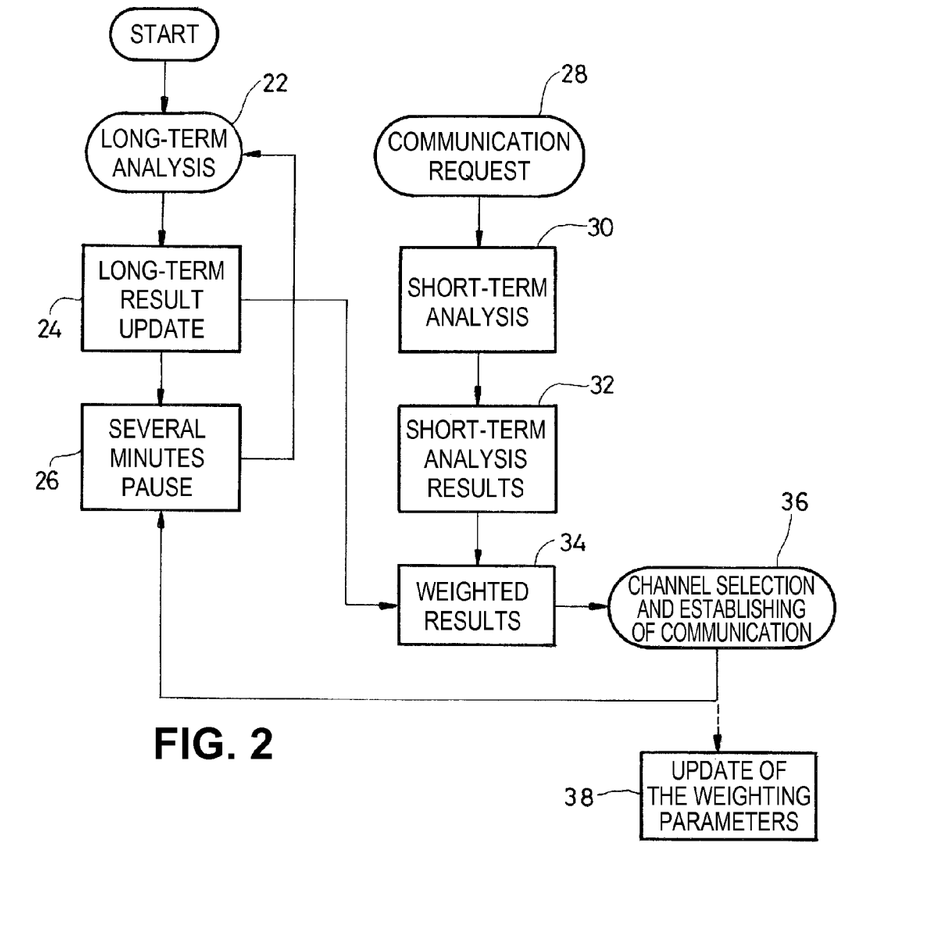
FIG. 2 is a flow chart illustrating steps for the selection of an RF channel based on a long-term analysis and a short-term analysis, according to one embodiment.
Figure 5:
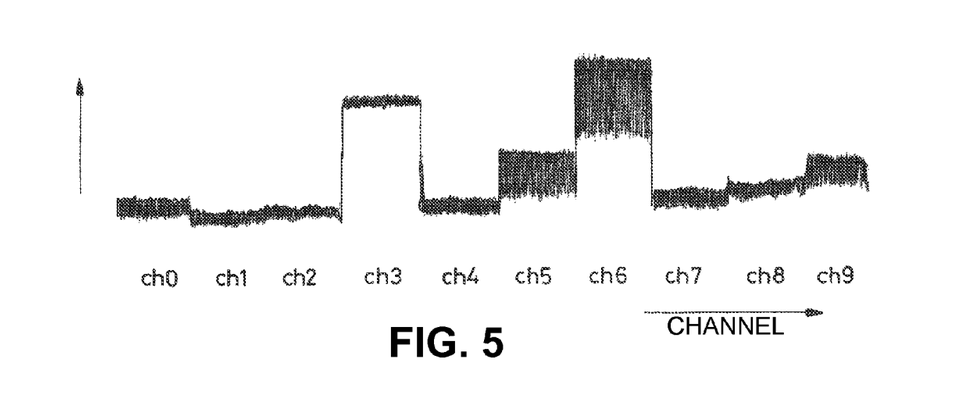
FIG. 5 illustrates exemplary signals measured over successive channels showing various signal levels and various types of interference.

FIG. 2 illustrates the operation of two types of analysis, namely a "long-term analysis" and a "short-term analysis." The long-term analysis performs scanning of the available channels at regular intervals in the absence of any request for establishing a new communication channel, whereas the short-term analysis performs scanning of a requested channel at the moment of the request for establishing a new communication. The long-term analysis (step 22) that is described in detail with reference to FIG. 5 is preferably performed at a regular interval, e.g., every fifteen minutes. This long-term analysis may be performed by a remote device, e.g., a base station, because it generally has available computing resource and energy to perform the analysis for all the scanned channels. However, it should be understood that the present invention could also be implemented mutatis mutandis from the device, although such an implementation is more critical especially in terms of energy consumption.

Most of the time, the base station remains inactive, with minimal power consumption but at regular intervals, it wakes up for an active period of time, e.g., a few seconds, to complete the long-term analysis (step 22) of the available channels. The results of this long-term analysis are stored and/or updated and compared to previous results (step 24), and the base station returns to a sleep state (step 26) and waits to be awakened for the next analysis period or upon receipt of an interruption as a request for communication.

Steps 22 and 24 for the long-term analysis and the storage of the analysis results involve successively scanning to the available channels and constructing a table for each scanned channel with a long-term indicator representative of the long-term availability of that channel. This table, once constructed, provides an overview of the "electromagnetic landscape" in the vicinity of the base station.

When a communication request is received (step 28), for example, from the active device, the base station scans the channels to determine one or more channels to use for data communication, for example, according to a Listen Before Talk (LBT) protocol prescribed by standard EN 301839. The base station then operates to perform a "short-term analysis" (step 30) of the same nature as the long-term analysis (step 22) that has previously been made in the absence of request. The results of the short-term analysis are stored (step 32) and combined (step 34) with the results of the long-term analysis, and a weighted result is obtained in the form of weighting parameters from the combined results of the short-term and long-term analysis. Using the weighted result, a channel is selected, and on the selected channel, the communication is established (step 36). For example, the weighting function depends on the number of successful data communication performed on a scanned channel, and these weights are modified over the time as the number of successful data communication varies.

The weighting parameters are updated (step 38) after establishing communication (step 36) to reflect whether the communication to the channel was successful established during this short-term scanning or, conversely, the communication has been interrupted or disturbed due to transmission errors or noises.

Figure 3:
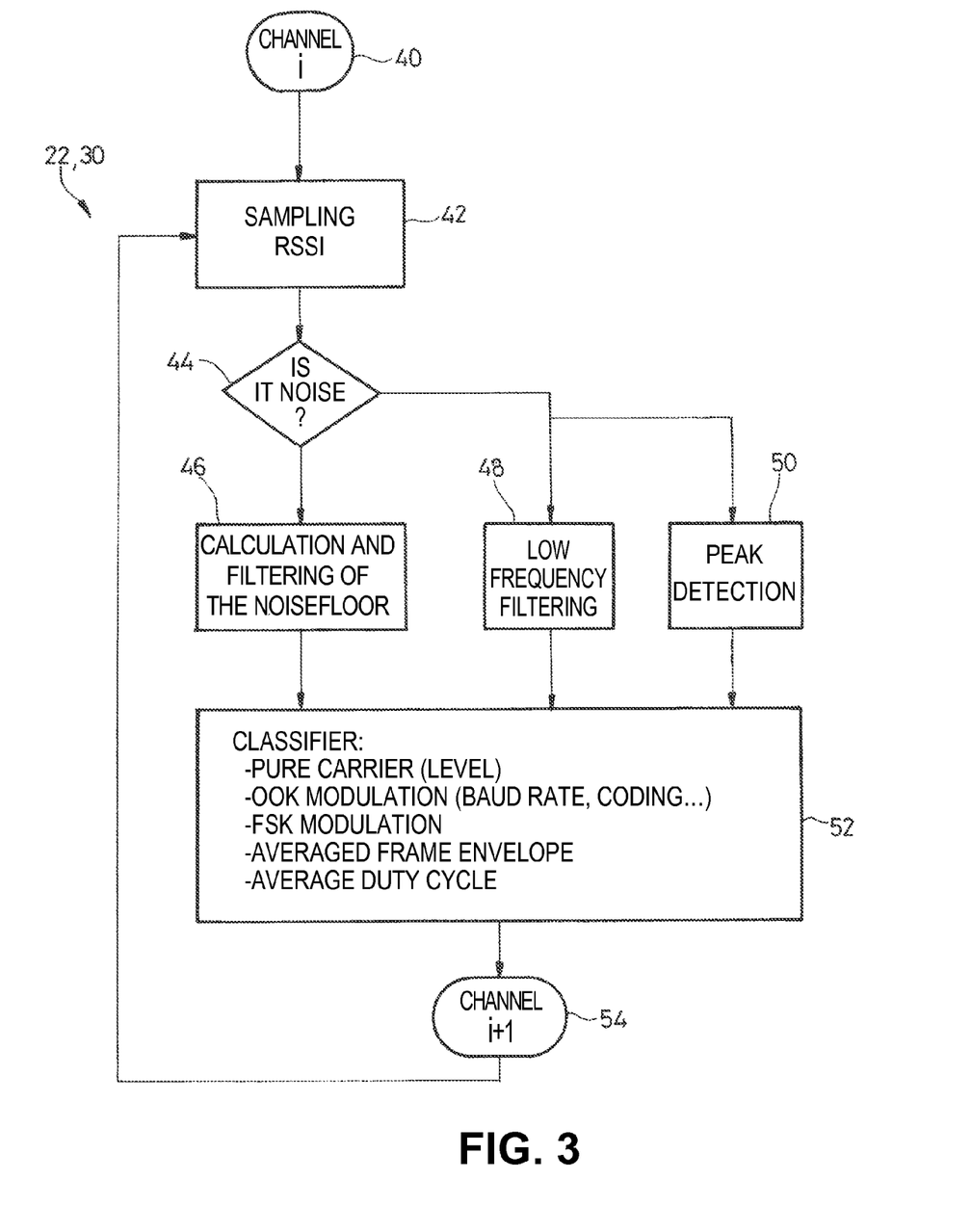
FIG. 3 is a flowchart illustrating the long term and short-term analysis of the flow chart of FIG. 2.

FIG. 3 illustrates a preferred method for the short-term and/or long-term analysis steps 22 and 30 in FIG. 2. For each channel i that is selected during the scan (step 40), the level of the received signal is sampled at reception (step 42). This signal level is referred to as Received Signal Strength Indicator (RSSI). The RSSI is compared to a relatively low threshold (step 44) in order to determine if the received signal is small enough to be considered as background noise. If so, a level of background noise is calculated from the RSSI (step 46) and is referred to as Noisefloor. A sliding average over a time window may be used for calculating the background noise to maximally filtering of the signal. For example, the time window for calculating the sliding average is 10 to 50 times longer than the average duration of the received signal. A new sample is introduced into this medium only if it appears as being at or above some signal level, that is to say, if it has a magnitude greater than that of the previous sample of background noise, according to the following equations:

$$\Delta_{i+1} = \frac{Average_i - Data_{i+1}}{windowLength}$$

$$Average_{i+1} = Average_i + \Delta_{i+1}$$

If the test 44 determines that the received signal does not contain background noise, the received signal is not used in computing and/or updating the Noisefloor level.

In this case, the received signal is determined to contain carrier signals beyond background noise, thus is subject to a low-frequency filtering (step 48) to generate an indicator RSSI_BF that is representative of the level of RSSI. The calculation in this step 48 is similar to that of the step 46, except that the time window is carefully selected to avoid filtering too much signal to extract the signal trend (e.g., the Shannon sampling frequency is approached without getting too close to it, to be consistent with the modulating frequency). The signal is further applied to a peak detection stage (step 50) for detecting a level peak occurring in the channel, even temporarily, in order to take into account an effect of signal saturation.

In one embodiment, the peak amplitude of the received signal is obtained as follows; If the new sample is higher than the previous one, the value is retained, otherwise the stored maximum value is simply reduced. This allows tracking of the peak and, by measuring the time during which this peak is higher than the average at step 50. One can estimate the peak amplitude and measure frequencies of repetition so as to determine whether there exists periodicity in the received signals or random signals are received.

Peak detection step 50 generates an indicator RSSI_Peak that is representative of the energy of the potential peak. In general, RSSI_Peak>RSSI_BF>Noisefloor. The three parameters Noisefloor, RSSI_BF and RSSI_Peak are combined at classifier 52 so as to perform signal classification and discriminate the type of the received signal: background noise only, pure carrier, modulated carrier (e.g., carrier with different modulation types), etc. This discrimination is further explained with reference to FIGS. 4a and 4b to illustrate examples of signals analyzed and discriminated by classifier 52.

Figure 4A:
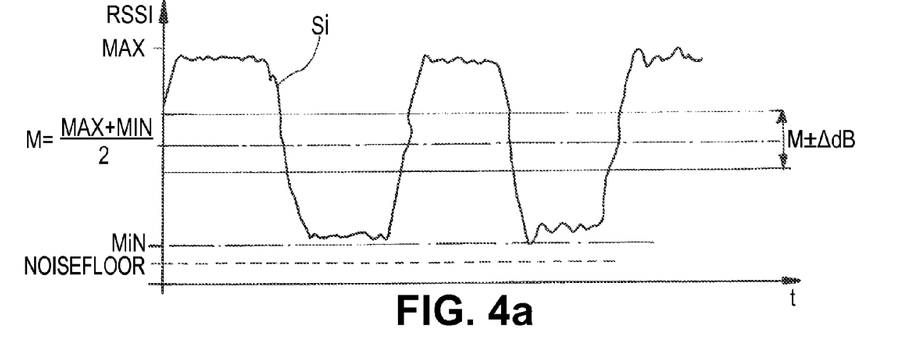
FIGS. 4a and 4b illustrate examples of signals analyzed and discriminated by the classifier of FIG. 2.

In FIG. 4a, received raw signal S1 is an amplitude modulated signal in the form of a succession of crenels. The maximum level MAX, the minimum level MIN and the average level M (M=(MAX+MIN)/2) of signal S1 are also obtained. A range, M±Δ, for example, at an interval of ±3 dB, around the average level M is also obtained.

Classifier 52 determines that the collected signal is actually an amplitude modulated signal if the following conditions are met:
  the maximum level MAX of the signal is higher than the background noise Noisefloor by a predetermined margin, for example, 3 dB;
  the number of digitized samples of the received signal which are at or in vicinity of the maximum level MAX corresponds (with a factor of uncertainty) to the number of samples that are at least at or in the vicinity of the minimum level MIN; it means that the signal samples are relatively equally distributed between the maximum and minimum of the received signal; and
  the average levels of the samples are in the range M±A around the average level M.

Figure 4B:
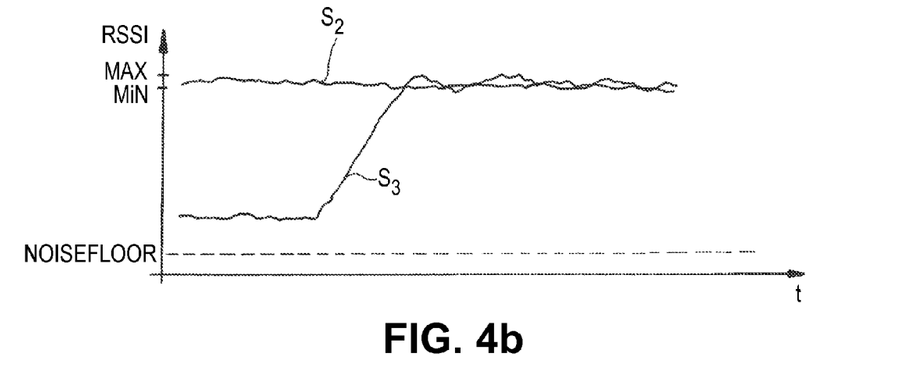

With reference to FIG. 4b, received raw signal S2 is a pure carrier or a frequency modulated signal. Classifier 52 determines that the collected signal contains such a carrier signal if the following conditions are met:
  The maximum level MAX of the signal is higher than the background noise Noisefloor by at least 3 dB (for example);
  The number of digitized samples of the received signal that are at or in the vicinity of the maximum level MAX corresponds (within a factor of uncertainty) to the number of samples that are at least at or in the vicinity of the minimum level MIN; it means that the signal samples are relatively equally distributed between the maximum and minimum of the signal; and
  The difference between the MAX and MIN levels of the signal is below a threshold, for example, 3 dB.

A further signal classification can be made to determine if the signal is being introduced (signal S3) or not (signal S2) during the sampling period by measuring a "filling rate" that represents the rate of the signal samples whose level is close to the maximum compared to the total number of signal samples.

Once the analysis of the signal on the channel i has been made, the analysis is performed for the next channel i+1 (step 54) until all the available channels are sampled.

In a normal operating condition of the active device, the parameter Noisefloor that represents the overall noise of the electronic circuits plus the ambient electromagnetic noise, does not vary abruptly. A sudden change in this parameter would come from a non-physical origin, for example, due to the deterioration of the electronic circuits and/or problems associated with the installation or a degradation of the device, at the end of life. An analysis on the changes in the parameter Noisefloor may be used to generate alerts.

Comparison of parameters RSSI_Peak and RSSI_BF allows evaluating the average duration of scramblers, for example, to distinguish between a single peak or a signal frame, or to identify the nature of the signal modulation: for example if RSSI_Peak is close enough to within a predetermined margin, RSSI_BF, it is considered that the signal contains a frequency shift keying (FSK) (i.e., frequency hopping discrete modulation) modulated signal, whereas if RSSI_Peak>RSSI_BF+Δ, Δ being another predetermined margin, it is considered that the signal contains an on-off keying (OOK) signal (i.e., all or no signal modulation).

In one embodiment, the present technique for signal analyses and comparisons is implemented fully or partly in hardware resources, for example, certain types of scramblers. The scramblers identify and learn the characteristics of the received signals over time and operate the signal classification by sorting the updated parameters.

From the results the analysis, an indicator that is representative of the availability of the channel is generated, for example, as a percentage or a rate of sampled signals to boost confidence in determining the nature and type of the received signals, in the short-term or long-term availability of the selected channel, depending on when the analysis is made.

FIG. 5 illustrates an example of signals measured on ten channels, ch0 to ch9. Channel ch3 shows a scrambler formed by a continuous pure carrier. Channel ch6 shows an OOK modulated scrambler that caused an overflow on channel ch5. Due to the high energy used for OOK modulation, the bandwidth of ch5 might be broader than ch6, thus a fraction of ch6 spectrum can be seen on ch5. These signals are considered to be correlated since they have the same signature in terms of the modulation rate and statistics, and the only difference is the maximum level.

Figure 6:
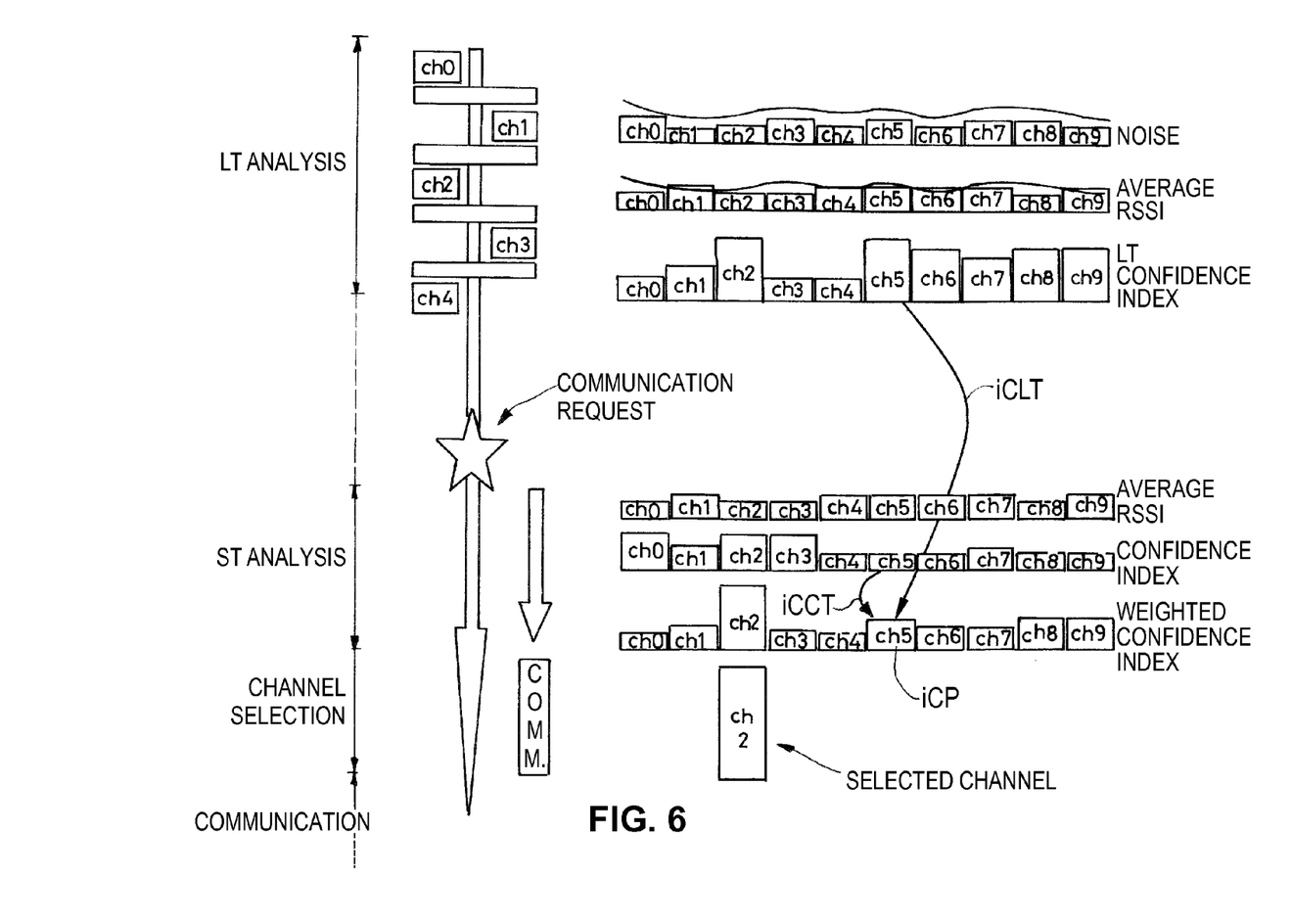
FIG. 6 schematically illustrates an exemplary channel selection process for RF telemetry based on successive phases of long term analysis, short term analysis.

FIG. 6 illustrates an exemplary channel selection process for RF telemetry based on successive steps of:
   a long-term analysis of the available channels repeated at a regular interval during periods of inactivity by a base station;
   a communication request;
   a short-term analysis of the available channels;
   a channel selection; and
   a start of communication.

In the long-term and short term analyses, the noise and the average RSSI are analyzed on each channel ch0 to ch9 in the present example to establish a confidence index, respectively, for a long term and a short term, respectively. The combination of the confidence indices in the long term (LT) and in the short-term (CT) are used to generate a confidence-weighted index iCP from the ten channels as schematized by the arrows referenced iCLT and iCCT. In one embodiment, the combination of the long-term and short-term indices is made through a sliding average, with varying time windows for the short-term analysis and for the long-term analysis. For channel chx of index x, the sliding averages for the long-term and short-term are calculated by the following equation, respectively:

$$\text{sliding\_average\_chx}(t+1) = \text{sliding\_average\_chx}(t) + (\text{sliding\_average\_chx}(t) - \text{chx\_CT})/\text{window\_CT},$$

and $$\text{sliding\_average\_chx}(t+1) = \text{sliding\_average\_chx}(t) + (\text{sliding\_average\_chx}(t) - \text{chx\_LT})/\text{window\_LT}$$

The long-term time window may be expressed by the multiplicity of the short-term time window, i.e., window_LT=N*window_CT. N allows adjusting the direct relationship between the two analyses and can be arbitrarily set as the temporal ratio between the two analyses. For example, if the short-term analysis is done once a day while the long-term analysis is done once per hour, then N=24.

In the example shown in FIG. 6, channel ch2 is selected because it has the highest weighted-confidence index. While other channels, such as channels ch0 and ch3, have an index of confidence in the short term at least as high, the long-term analysis showed that these channels have a long-term confidence index less than that of channel ch2, so they are eliminated prior to the establishment of communication in the process of channel selection. In the present example, the weighted function is represented by the height of the bar graph, i.e.:

selected channel=weighted confidence index*confidence index*average RSSI.

One skilled in the art will understand that the present invention can be practiced by other than the embodiments disclosed herein, which are provided for the purposes of illustration only but not of limitation.

The invention claimed is:

1. A method for searching and selecting a communication channel among a plurality of channels, prior to the establishment of an RF telemetry link between a remote device and an active medical device, comprising:
   establishing a communication in progress with the remote device;
   during an absence of a communication request from the remote device, periodically conducting a first scanning and analysis of said plurality of channels and, for each channel, determining and storing a first indicator representative of a long-term availability;
   receiving the communication request from the remote device;
   in response to the communication request, conducting a second scanning and analysis of said plurality of channels and, for each channel, determining and storing a second indicator representative of a short-term availability; and
   selecting the communication channel from the plurality of channels based on said first and second indicators,
   wherein said first indicator is a long-term indicator (iCLT) representative of the long-term availability,
   the second indicator is a short-term indicator (iCCT) representative of the short-term availability,
   a weighted short-term indicator is generated by weighting of the short-term indicator by the long-term indicator, and
   said communication channel is selected based on the weighted short-term indicator.

2. The method of claim 1, wherein said first or second analysis further comprises comparing a signal level (RSSI) of each channel of said plurality of channels to a predetermined threshold level of baseline noise.

3. The method of claim 2, wherein said first or second analysis further comprises, for each channel whose signal level is above the predetermined threshold level of baseline noise, discriminating a signal type by differentiating a data frame signal and a noise signal.

4. The method of claim 3, wherein the step of discriminating a signal type further comprises:
   low-pass filtering unfiltered signals over a temporal window of a predetermined duration;
   comparing at least one filtered signal and at least one unfiltered signal; and
   generating a first indicator of signal type based on the comparison of the at least one filtered signal and the at least one unfiltered signal.

5. The method of claim 4, wherein the step of discriminating a signal type further comprises:
   detecting a peak signal level;
   comparing the peak signal level and the at least one filtered signal; and
   generating a second indicator of signal type based on the comparison of the peak signal level and the at least one filtered signal.

6. An apparatus for communication with a remote device comprising:
   an attenuator for receiving signals on a plurality of channels from the remote device;
   a channel filter for selectively receiving signals on a selected channel of the plurality of channels; and
   a means for searching and selecting a communication channel among the plurality of channels, prior to the establishment of an RF telemetry link with the remote device,
   wherein the means for searching and selecting the communication channel prior to the establishment of the RF telemetry link comprises:
      means for a first analysis, the first analysis being periodically conducted for each channel of said plurality of channels;
      means for determining and storing a first indicator representative of a long-term availability for each channel of the plurality of channels;
      means for a second analysis, the second analysis being conducted for each channel of said plurality of channels in response to a communication request from the remote device;
      means for determining and storing a second indicator representative of a short-term availability for each channel of the plurality of channels; and
      means for selecting the communication channel from said plurality of channels based on said first and second indicators,
   wherein said first indicator is a long-term indicator (iCLT) representative of the long-term availability,
   wherein the second indicator is a short-term indicator (iCCT) representative of the short-term availability,
   wherein a weighted short-term indicator is generated by weighting of the short-term indicator by the long-term indicator, and
   wherein said communication channel is selected based on the weighted short-term indicator.

7. The apparatus of claim 6, wherein said means for the first or second analyses further comprises means for comparing a signal level (RSSI) of each channel of said plurality of channels to a predetermined threshold level of baseline noise.

8. The apparatus of claim 7, wherein said means for the first or second analyses further comprises, for each channel whose signal level is above the predetermined threshold level of baseline noise, means for discriminating a signal type by differentiating a data frame signal and a noise signal.

9. The apparatus of claim 8, wherein the means for discriminating a signal type further comprises:
   a low-pass filter for filtering unfiltered signals over a temporal window of a predetermined duration;
   a comparator for comparing at least one filtered signal and at least one unfiltered signal; and
   means for generating a first indicator of signal type based on the comparison of the at least one filtered signal and the at least one unfiltered signal.

10. The apparatus of claim 9, wherein the means for discriminating a signal type further comprises:
    a peak signal level detector configured to detect a peak signal level;
    a comparator for comparing the peak signal level and the at least one filtered signal; and
    means for generating a second indicator of signal type based on the comparison of the peak signal level and the at least one filtered signal.

* * * * *